(12) United States Patent  (10) Patent No.: US 11,857,742 B2
Li et al.  (45) Date of Patent: Jan. 2, 2024

(54) BALLOON CATHETER

(71) Applicant: SINO Medical Sciences Technology Inc., Tianjin (CN)

(72) Inventors: Zhonghua Li, Tiajin (CN); Tianzhu Li, Tianjin (CN); Xueying Wang, Tianjin (CN)

(73) Assignee: SINO Medical Sciences Technology Inc., Tianjin (CN)

( * ) Notice: Subject to any disclaimer, the term of this patent is extended or adjusted under 35 U.S.C. 154(b) by 313 days.

(21) Appl. No.: 17/002,920

(22) Filed: Aug. 26, 2020

(65) Prior Publication Data

US 2021/0060312 A1 Mar. 4, 2021

(30) Foreign Application Priority Data

Aug. 28, 2019 (CN) .......................... 201910800643.7

(51) Int. Cl.
A61M 25/10 (2013.01)
A61M 25/01 (2006.01)

(52) U.S. Cl.
CPC ..... A61M 25/10 (2013.01); A61M 2025/0183 (2013.01); A61M 2025/1004 (2013.01); A61M 2025/1075 (2013.01); A61M 2025/1079 (2013.01); A61M 2025/1093 (2013.01)

(58) Field of Classification Search
CPC ............ A61M 25/005; A61M 25/0052; A61M 25/0169; A61M 25/0172; A61M 25/10; A61M 25/1006; A61M 25/104; A61M 2025/0042; A61M 2025/0098;

(Continued)

(56) References Cited

U.S. PATENT DOCUMENTS

2003/0125709 A1* 7/2003 Eidenschink ..... A61M 25/0662
604/524
2003/0208221 A1* 11/2003 El-Nounou ......... A61M 25/104
606/191

(Continued)

FOREIGN PATENT DOCUMENTS

CN 109331322 A * 2/2019 .......... A61M 25/104
WO WO-2018176064 A2 * 9/2018 ....... A61B 17/12036

Primary Examiner — Kami A Bosworth
(74) Attorney, Agent, or Firm — Locke Lord LLP; Nicholas J. DiCeglie, Jr.

(57) ABSTRACT

The present application relates to a balloon catheter, which is a rapid exchange structure and has a balloon catheter body and a hub, wherein the balloon catheter body has a push member, a transition member, a balloon loading member, a balloon, a imaging mark and a tip head, the balloon loading member comprises an outer tube and an inner tube, a distal end of the handle is connected with a proximal end of the push member, a proximal end of the transition member extends from a distal end of the push member, a distal end of the transition member is nested inside a proximal end of the outer tube of the balloon loading member, the balloon loading member loads the balloon, the tip head is provided on a distal end of the balloon, the imaging mark is provided on the balloon loading member, characterized in that the balloon has a wall thickness of 10-15 microns, the balloon has a nominal dilation pressure of 3-4 atm, and the balloon catheter has a rated burst pressure of is 10-12 atm.

9 Claims, 2 Drawing Sheets

(58) Field of Classification Search
CPC .. A61M 2025/0183; A61M 2025/1004; A61M 2025/1043; A61M 2025/1079
See application file for complete search history.

(56) References Cited

U.S. PATENT DOCUMENTS

| | | | | |
|---|---|---|---|---|
| 2016/0045717 A1* | 2/2016 | Issendorff | ............... | A61L 29/02 |
| | | | | 604/103.01 |
| 2018/0193042 A1* | 7/2018 | Wilson | .............. | A61M 25/0045 |
| 2019/0344053 A1* | 11/2019 | Wang | ................... | B29D 22/023 |

\* cited by examiner

BALLOON CATHETER

CROSS-REFERENCE TO RELATED APPLICATIONS

This application claims priority to Chinese Patent Application No. 201910800643.7, filed in the Chinese Intellectual Property Office on Aug. 28, 2019, which application is hereby incorporated herein by reference.

TECHNICAL FIELD

The present application relates to a balloon catheter for balloon dilatation. In particular, the present application relates to a balloon catheter with low dilatation pressure and high trafficability and transportability to adapt to a specific application such as dilatation of intracranial vessels.

BACKGROUND ART

Acute Ischemic Stroke (AIS) is a common and frequently occurring disease in clinic, which has characteristics of high incidence rate and high mortality. Now there are 15 million new stroke patients in the world every year, and 87% of them are acute ischemic stroke. Every year, more than 5 million people die of acute ischemic stroke, and another 5 million people suffer from irreversible disability due to acute ischemic stroke. About 1.25 million stroke patients are added every year in Europe, and more than 650,000 people die of stroke every year. About 800,000 stroke patients are added annually in the United States, of which about 700,000 are acute ischemic stroke, which is the fourth leading cause of death in the United States. According to the results of China's third survey of national cause of death, the stroke has become the first cause of death in China, and the incidence rate of stroke in China ranks first in the world. Every year, the number of stroke deaths is more than 2 million, the mortality rate is 4-5 times of that of European and American countries, 3.5 times of that of Japan, and the annual growth rate is 8.7%. In addition, stroke has a high rate of disability and recurrence. The clinical results showed that the death rate of stroke was 20%-30%, most of the survivors had sequelae, about 75% of them lost their ability to work in varying degrees, and about 40% of them were severely disabled.

At present, the treatment methods for acute ischemic stroke mainly include basic treatment, thrombolytic therapy, interventional device therapy and nerve cell protection therapy, etc., among which thrombolytic therapy and interventional device therapy are two currently common treatment methods. Thrombolytic therapy includes arterial thrombolysis, intravenous thrombolysis and arteriovenous combined thrombolysis, mainly using tissue-based fibrin activator, urokinase and other drugs for thrombolysis. The best time window for treatment is 3-6 hours. However, statistical data shows that only 2%-4% of the patients received treatment within 3 hours of onset and only 15% within 6 hours. The vast majority of patients have missed the best treatment time at the time of visit. Compared with thrombolytic therapy, interventional device therapy for AIS is less limited by the time of onset and other inclusion criteria.

In the treatment of complex intracranial artery stenosis, pure balloon dilatation has a great advantage. Compared with the coronary artery vessels, the intracranial vessels are tortuous and small and complex in structure. Therefore, the intracranial interventional surgery requires higher performance of the balloon catheter products, that is, the products need to have excellent delivery performance to smoothly cross the tortuous intracranial vessels to reach the narrow lesions, and safely and effectively expand and withdraw from the body. There is no muscle tissue protection outside the intracranial vessels, the vessels are tortuous and soft, easy to be damaged, so it is not suitable for over expansion and long-term implantation of stents; nor is the blood vessel of coronary artery subject to corresponding stress due to beating of the heart, and the blood vessels in the intracranial lesions will not be easily retracted after expansion. And simple balloon dilation does not need more pressure, just right. Moderate dilation is more beneficial to the postoperative recovery of the blood vessels in the lesion.

The balloon catheter of the prior art is not particularly suitable for the treatment of intracranial artery related lesions. In clinical practice of the interventional treatment of intracranial vessels, if doctors use a common balloon under a condition below the nominal pressure, it may not be able to fully expand; if they use a common balloon under the nominal pressure, it may easily cause damage to the blood vessels.

The information disclosed in the part of background art of the application is only intended to deepen the understanding of the general background technology of the application, and shall not be deemed to recognize or imply in any form that the information constitutes the prior art which is known to those skilled in the art.

SUMMARY OF THE INVENTION

In order to solve the problems existing in the prior art, the purpose of the present application is to provide a balloon catheter with low dilation pressure, which is suitable for dilating intracranial stenosis vessels and improving the success rate of minimally invasive surgery.

The purpose of the present application is also to provide a balloon catheter with high trafficability and transportability.

The present application relates to a balloon catheter, which is a rapid exchange structure and has a balloon catheter body and a hub, wherein the balloon catheter body has a push member, a transition member, a balloon loading member, a balloon, a imaging mark and a tip head, the balloon loading member includes an outer tube and an inner tube, a distal end of the hub is connected with a proximal end of the push member, a proximal end of the transition member extends from a distal end of the push member, a distal end of the transition member is nested inside a proximal end of the outer tube of the balloon loading member, the balloon loading member loads the balloon, the tip head is arranged on a distal end of the balloon, the imaging mark is arranged on the balloon loading member, characterized in that the balloon has a wall thickness of 10-15 microns, the balloon has a nominal dilation pressure of 3-4 atm, and the balloon catheter has a rated burst pressure of is 10-12 atm.

According to a preferred embodiment of the present application, the nominal dilation pressure of the balloon is 3 atm.

According to a preferred embodiment of the present application, the rated burst pressure of the balloon catheter is 12 atm.

According to a preferred embodiment of the present application, the balloon adopts a folding structure of two folded wings, three folded wings or five folded wings, with a crossing profile, i.e., the passing outer diameter, of 0.66 mm-0.90 mm.

According to a preferred embodiment of the present application, the crossing profile i.e., the passing outer diameter, of the balloon is 0.78 mm.

According to a preferred embodiment of the present application, the length of a coaxial structure of a hose section of the balloon catheter is 300-400 mm.

According to a preferred embodiment of the present application, the push member is composed of a metal-based hypo tube or a braided tube with a cavity structure, the push member has a length of 800 mm-1400 mm, an outer diameter of 0.40 mm-0.70 mm, and a thickness of 0.05 mm-0.15 mm, the transition member is selected from a hypo tube with a screw structure and a core wire with a variable diameter structure, and materials of the outer tube and the inner tube are selected from a block polyether amide elastomer, nylon, polyurethane or HDPE.

According to a preferred embodiment of the present application, the transition member is a spiral cut structure made of metal, and an end of the transition member forms a shovel like structure with gradual size change.

According to a preferred embodiment of the present application, the imaging mark is arranged on the inner tube, and material of the imaging mark is selected from gold, platinum, platinum iridium alloy and tungsten rhenium alloy.

The present application may have other features and advantages, which will become apparent or be stated in detail by the drawings incorporated herein and the subsequent specific embodiments, which are jointly used to explain the specific principles of the present application.

Figure 1:
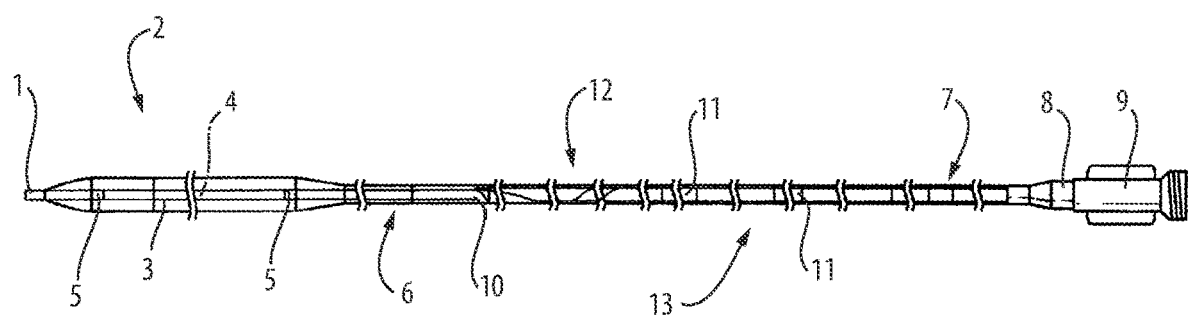
FIG. 1 is a schematic diagram of an exemplary embodiment of the balloon catheter of the present application.

DESCRIPTION OF REFERENCE NUMBERS 1) tip head;
2) balloon protective sheath;
3) balloon;
4) inner tube;
5) imaging mark;
6) outer tube;
7) hypotube;
8) heat shrink tube;
9) hub;
10) rapid exchange port;
11) dimension marking;
12) transition member;
13) push member.

DETAILED DESCRIPTION OF EMBODIMENTS

Next, a detailed reference will be made to embodiments of the present application, examples of which are shown in the accompanying drawings and described below. Although this application will be described in combination with exemplary embodiments, it should be understood that this description is not intended to limit this application to those exemplary embodiments. On the contrary, the present application is intended to cover not only these exemplary embodiments, but also various alternations, modifications, equivalents and other embodiments that may be included in the spirit and scope of the present application as defined by the appended claims.

Hereinafter, various exemplary embodiments of the invention will be described more specifically with reference to the accompanying drawings.

First, in order to describe the embodiments of the invention more clearly, "proximal end" and "distal end" are defined according to common terms in the field of interventional medicine.

When a physician carries out normal operations with a hand-held tool or device in the face of a patient, and the tool or device is located between the physician and the patient, the end close to the physician is called the "proximal end", while the end away from the physician (the end close to the patient) is called the "distal end".

The above definitions of "proximal end" and "distal end" are only for the convenience of describing embodiments of the invention, and do not limit structures of the invention. Alternatively, the "proximal end" may also be referred to as the first end, while the "distal end" may be referred to as the second end accordingly.

According to an exemplary embodiment of the present application, a balloon catheter of a rapid exchange type is provided, which includes a hub 9 and a balloon catheter body, wherein the balloon catheter body is composed of a push member, a transition member, a balloon loading member, a balloon 3, a imaging mark 5 and a tip head 1. The distal end of the hub 9 is connected with the proximal end of the push member, the proximal end of the transition member extends from the distal end of the push member, and the distal end of the transition member is nested inside the proximal end of the outer tube 6 of the balloon loading member. The balloon loading member is capable of loading the balloon 3. Specifically, the proximal end of the balloon 3 is nested and fixed outside the distal end of the outer tube 6. The inner tube 4 is nested in the inner side of the outer tube 6 from the rapid exchange port 10 to form a coaxial structure, and the inner tube 4 extends so that its distal end exceeds the distal end of the outer tube 6. The distal end of the balloon 3 is provided with a tip head 1. The distal end of the inner tube 4, the distal end of the balloon 3 and the proximal end of the tip head 1 are fixed so that the distal end of the balloon 3 is located between the distal end of the inner tube 4 and the proximal end of the tip head 1. For example, laser welding, hot-air fusion welding, physical bonding, etc. are the fixing ways among various parts, preferably laser welding. The imaging mark 5 is arranged on the inner tube 4 of the balloon loading member.

Various components of the balloon catheter body are connected and fixed by laser welding, heat sealing and other processes. In one embodiment, the hub 9 and the balloon catheter body are fixed and strengthened by a heat shrink tube 8.

Further, the balloon catheter body is coated with a coating that increases lubrication and reduces vascular damage, such as a super lubricated hydrophilic coating. The coating materials include: one or more of PTFE, PU, polyvinyl pyrrolidone (PVP), polyvinyl pyrrolidone containing coupling iodine, polyvinyl alcohol (PVA), polyethylene oxide (PEO) or polyethylene glycol (PEG).

The wall of the balloon 3 of the exemplary embodiment of the present application is thinner and softer than that of the prior art by adopting specific materials, structures and processes (such as electric heating forming process, etc.).

For example, the balloon 3 is made of a softer material selected from block polyether amide elastomer, nylon, polyurethane, polyester, polyacylamide compound, etc. The single wall thickness of the balloon 3 is about 10-15 microns, such as 10 microns, 11 microns, 12 microns, 13 microns, 14 microns and 15 microns. In contrast, the wall thickness of the balloon of the prior art is 20-25 microns. For the balloon of the same specification, the balloon 3 of the exemplary embodiment of the present application deflects to about 45 degrees in the upright state, which is much larger than that of the balloon of the prior art. Owe to the thinner and softer wall, the nominal dilation pressure (NP) of the balloon of the application can be set as 3-4 atm, such as 3 atm, 3.2 atm, 3.4 atm, 3.6 atm, 3.8 atm, 4 atm, preferably 3 atm. In contrast, the nominal dilation pressure of the balloon of the prior art is set as 6-8 atm. For the balloon catheter of the same specification, the balloon size achieved by dilating the present balloon catheter under 3 atm is the same as or similar to that achieved by dilating the balloon catheter of the prior art to 6-8 atm. In order to ensure the safety performance during the use of the balloon catheter, the rated burst pressure (RBP) of the balloon catheter is relatively high, which is set as 10-12 atm, such as 10 atm, 10.5 atm, 11 atm, 11.5 atm, 12 atm, preferably 12 atm.

In order to achieve relatively small nominal pressure and the rated burst pressure sufficient for safe space, special process should be adopted to form the balloon. First of all, it is necessary to select an appropriate initial tube, which requires the outer diameter of the tube to be 0.5 mm-1.4 mm, the wall thickness to be 0.20 mm-0.60 mm, and the concentricity to be 80%-100%. A suitable balloon molding mold is selected, such as a mold made from beryllium copper alloy, copper, PEEK and other materials. Through several steps, such as two steps, after heating the tube and reaching the glass transition temperature, the tube is inflated and stretched to shape in the mold. It needs to be stretched many times (for example, 2-4 times) to form different parts, and finally cooled and shaped. In the process of balloon molding, the tube has a stretching rate of 150%-400%, and an inflation ratio of 2.5-4.0. Products having different specifications have their own unique molding parameters, which are a combination of factors such as temperature of 80-150° C., pressure of 10-40 bar, stretching distance of 10-25 mm, setting time of 10-25 s, stretching force of 20-60 N in a period of time.

The following is a table summarizing the parameters of the balloon realized by several embodiments of the combination of different factors according to the process of the application obtained from experiments, as well as comparison with the balloon of the prior art.

TABLE 1

| | Initial tube | | | Molding parameters | | | | | | | | Balloon parameters | | |
|---|---|---|---|---|---|---|---|---|---|---|---|---|---|---|
| No. | Outer diameter (mm) | Wall thickness (mm) | Concentricity (%) | Temperature in step 1 (° C.) | Temperature in step 2 (° C.) | Stretching times | Inflation 1 (bar) | Inflation 2 (bar) | Stretching distance (mm) | Setting time (s) | Stretching force (N) | Wall thickness (μm) | NP (atm) | RBP (atm) |
| 1 | 0.50 | 0.20 | 100 | 95 | 125 | 3 | 10 | 35 | 14 | 10 | 20 | 10 | 3 | 12 |
| 2 | 0.78 | 0.33 | 100 | 95 | 130 | 3 | 10 | 30 | 20 | 15 | 40 | 11 | 3 | 12 |
| 3 | 0.85 | 0.37 | 100 | 85 | 135 | 2 | 10 | 32 | 15 | 15 | 40 | 11 | 3 | 12 |
| 4 | 0.91 | 0.40 | 100 | 90 | 140 | 2 | 10 | 30 | 15 | 12 | 40 | 13 | 4 | 12 |
| 5 | 0.91 | 0.40 | 100 | 90 | 135 | 3 | 10 | 30 | 12 | 10 | 40 | 12 | 3 | 12 |
| 6 | 0.91 | 0.40 | 100 | 85 | 140 | 4 | 10 | 32 | 10 | 20 | 40 | 12 | 3 | 12 |
| 7 | 1.05 | 0.40 | 95 | 95 | 135 | 3 | 10 | 32 | 18 | 12 | 40 | 12 | 3 | 12 |
| 8 | 1.15 | 0.44 | 80 | 95 | 140 | 3 | 10 | 40 | 16 | 25 | 40 | 12 | 4 | 12 |
| 9 | 1.40 | 0.60 | 100 | 80 | 150 | 3 | 10 | 40 | 25 | 12 | 60 | 15 | 3 | 12 |
| Reference | 0.79 | 0.28 | 100 | / | 85 | 2 | / | 26 | / | 20 | 10 | 20 | 6 | 12 |

With high flexibility and low nominal pressure of the balloon 3, the balloon should be inflated slowly compared with the balloon in the prior art.

After the balloon 3 is folded, its folded wing is in a spiral shape to reduce its outer diameter. The balloon 3 is formed by folding with two folded wings, three folded wings or five folded wings. The folding structure cooperates with the thin and soft wall of the balloon, so that the balloon 3 of the application has a suitable crossing profile, i.e., a suitable passing outer diameter, and good refolding, and can be inflated several times. Compared with the balloon of the prior art, the balloon 3 of the exemplary embodiments of the present application has a smaller crossing profile, which ranges from 0.66 mm to 0.90 mm, such as 0.66 mm, 0.72 mm, 0.78 mm, 0.84 mm and 0.90 mm.

The balloon 3 also has certain shape memory.

The balloon loading member is composed of an outer tube 6 and an inner tube 4. The outer tube 6 and the inner tube 4 can be a single layer or a multi-layer structure, so as to realize the function of transporting balloon and work stably under a certain pressure.

The materials of the outer tube 6 and the inner tube 4 are block polyether amide elastomer, nylon, polyurethane or high-density polyethylene and other polymer materials or composite tubes.

The hardness of the outer tube 6 and the inner tube 4 can be kept unchanged or orderly varied from the proximal end to the distal end.

The outer diameter of the outer tube 6 is 0.80 mm-1.00 mm, for example, 0.80 mm, 0.90 mm, 1.00 mm, preferably 0.90 mm. The inner diameter of the outer tube 6 is 0.60-0.90 mm, for example, 0.60 mm, 0.70 mm, 0.80 mm, 0.90 mm, preferably 0.70 mm. The length of the outer tube 6 is 360 mm-480 mm, for example 360 mm, 400 mm, 440 mm, 480 mm, preferably 450 mm. The outer diameter of the inner tube 4 is 0.55 mm-0.65 mm, for example, 0.55 mm, 0.60 mm, 0.65 mm, preferably 0.57 mm. The inner diameter of the inner tube 4 is 0.40 mm-0.45 mm, for example, 0.40 mm, 0.45 mm, 0.50 mm, preferably 0.42 mm. The length of the inner tube 4 is 280 mm-380 mm, for example, 280 mm, 315 mm, 380 mm, preferably 300 mm.

The inner tube 4 is provided with a imaging mark 5. The material of the imaging mark 5 is gold, platinum, platinum iridium alloy, tungsten rhenium alloy, etc.

Compared with the balloon catheter of the prior art, the structural design and assembly of the application are improved and optimized. The length of the coaxial structure of the hose section from the tip head 1 to the rapid exchange port 10 is lengthened, and the outer diameter, length dimension and gradual changing structure of the transition member are designed to transfer the operation of the end of the hub 9 to the tip head 1 to the most extent, without losing the overall flexibility. The assembling and combination of various connecting parts are more optimized to achieve smooth transition and smoother force transmission. Thus, the balloon catheter of the present application can smoothly reach the lesion in the tortuous and narrow intracranial vessels.

In order to improve the intravascular transporting performance of the product to a greater extent, the length of the coaxial structure of the hose section of the balloon catheter is lengthened to 300-400 mm, such as 300 mm, 320 mm, 340 mm, 360 mm, 380 mm, 400 mm, preferably 310 mm. The length of the distal hose section of the balloon of the prior art is 200-250 mm. The effective length of the present application is about 50-100 mm longer than that of the prior art, so that the overall effective length reaches 1450-1650 mm, preferably 1550 mm.

The transition member includes, but is not limited to, one structure or combination of structures of a spring, a hypo tube having screw structure and a core wire having variable diameter structure. The spring or screw can be of variable pitch structure.

Figure 2:
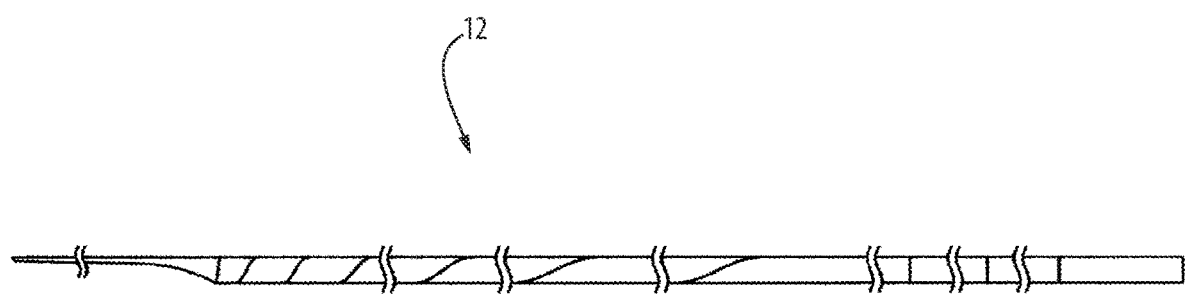
FIG. 2 is a partial enlarged view of an exemplary embodiment of the balloon catheter of the present application, in particular showing a transition member.

According to an exemplary embodiment shown in FIG. 2, the transition member is a spiral cut structure made of metal. In other words, the main body of the transition member is in tubular shape, and the tube is cut along the spiral line. Preferably, the pitch of the spiral line gradually decreases from the end connected with the push member to the end of the balloon 3. At one end of the balloon 3, the end of the transition member forms a shovel like structure having gradually changing size.

Compared with the balloon catheter of a coaxial structure, the balloon catheter having a rapid exchange structure is more convenient and efficient to use, but the conductivity of force decreases with respect to the coaxial structure because of dispersion of the rapid exchange port 10. However, properly increasing the length of the coaxial structure segment is beneficial for the balloon and the whole hose section to deliver and reach lesion in the blood vessel. The combination of the relatively long hose section of the balloon and the spiral metal reinforcing section of the application can greatly improve the transporting performance of the whole product in the intracranial vessels. In vitro laboratory data, it show that the thrust and withdrawal force required for the delivery of the balloon catheter in simulated blood vessels are 30%-40% less than that of the balloon of the prior art, which can achieve or even be superior to the transporting performance of the coaxial balloon catheter.

The push member is composed of tubes such as a metal-based hypo tube 7 and a braided tube with a cavity structure, which is characterized in that the length range of the tube is 800 mm-1400 mm, the preferred range is 1150 mm-1250 mm, such as 1150 mm, 1200 mm, 1250 mm. The tube can be of the same diameter or variable diameter structure, which only needs to ensure having appropriate support strength, good pushing performance and the fluid in the cavity flowing smoothly under a certain pressure, with an outer diameter of 0.40 mm-0.70 mm, and a thickness of 0.05 mm-0.15 mm.

Preferably, the outer wall of the tube of the push member has a dimension marking 11.

The balloon catheter according to the application can maintain the overall mechanical balance, so that the force can be accurately transmitted from the hub 9 to the working end of the balloon, so that it has good pushing performance and can be smoothly transmitted to the intracranial vascular site. At the same time, it has excellent flexibility and trafficability, so that the balloon catheter can easily reach the brain through a tortuous vascular pathway to carry out treatment.

The design of nominal dilation pressure and rated burst pressure is based on the characteristics of intracranial vessels. As there is no muscle tissue support protection outside the intracranial vessels, the vessels are tortuous and soft, easy to be damaged, so it is not suitable for over dilation and long-term stent implantation. Therefore, the interventional treatment of intracranial vessels is more conservative than that of coronary intervention treatment to ensure the safety of patients during operation. The higher the pressure, the greater the damage to blood vessels, and many of the vascular intimal damage cannot be evaluated by imaging. On the other hand, the intracranial vessels are not like the vessels of coronary artery which will be stressed correspondingly due to the beating of the heart, the intracranial lesion vessels will not be easily retracted after being dilated. Simple balloon dilation does not need much pressure, just right. To achieve the purpose of dilating vascular lesions under low pressure will greatly reduce the pulling and damage to blood vessels, and provide more security and safety for patients and doctors. The thinner and softer wall of the balloon used in this application allows to set less dilation pressure, which means that the balloon can contact with the wall of blood vessels under a lower pressure and give a proper radial action intensity, which can realize moderate dilation of the lesion blood vessel, and reduce or even eliminate the damage to the blood vessels to a greater extent. The higher rated burst pressure can ensure that the balloon will not burst in the process of continuous pressure rise, so as to avoid unnecessary damage to the blood vessels.

Similarly, to the characteristics of tortuosity and softness of the intracranial vessels, the balloon catheter suitable for this application should have high trafficability and transportability. The balloon used for the balloon catheter of the present application has a folding structure, and wall of the balloon is thin and soft, and is further coated with a coating for lubrication, providing better trafficability. In addition, the balloon hose section used in the balloon catheter of the present application is relatively long, which is combined with the spiral metal reinforcing section to provide better transportability. In the simulated use test in vitro, the transportability. performance of the catheter in this application is 30%-40% higher than that of the ordinary intracranial balloon catheter. In conclusion, the application further reduces damage to blood vessels.

In the interventional treatment using the balloon catheter of the present application, the lesion position in the blood vessel is first determined by angiography, then the catheter sheath is fed into the blood vessel from the femoral artery or brachial artery, the guide wire is penetrated into the catheter sheath and passed through the lesion, the balloon catheter is introduced into the blood vessel, and the balloon catheter is pushed along the guide wire to the lesion site, and the hub is connected with an inflation device, the balloon cavity is filled with an appropriate volume of contrast medium, the balloon dilates to open the blocked lesions, the balloon catheter is deflated, the balloon changes from a filled state to a negative pressure state, and then the balloon catheter is withdrawn from the body.

The foregoing description of the specific exemplary embodiment of the present application is for the purpose of explanation and description. The above description is not intended to be exhaustive, or that the application is strictly limited to the specific form disclosed. Obviously, many changes and modifications may be made according to the above teachings. The purpose of selecting and describing exemplary embodiments is to explain the specific principles and practical applications of the present application, so that other technicians in the art can realize and utilize various exemplary embodiments of the present application and various selections and modifications. The scope of this application is intended to be limited by the appended claims and their equivalents.

The invention claimed is:

1. A balloon catheter, comprising a rapid exchange structure having a balloon catheter body and a hub, wherein the balloon catheter body has a push member, a transition member, a balloon loading member, a balloon, an imaging mark and a tip head, the balloon loading member comprises an outer tube and an inner tube, a distal end of the hub is connected with a proximal end of the push member, a proximal end of the transition member extends from a distal end of the push member, a distal end of the transition member is nested inside a proximal end of the outer tube of the balloon loading member, the balloon loading member loads the balloon, the tip head is provided on a distal end of the balloon, the imaging mark is provided on the balloon loading member, characterized in that the balloon has a wall thickness of 10-14 microns, the balloon has a nominal dilation pressure of 3-4 atm, and the balloon catheter has a rated burst pressure of 10-12 atm, and the balloon can deflect to an angle of 45 degrees in upright state, wherein the balloon is manufactured from an initial tube having an outer diameter of 0.5 mm-1.4 mm, and a wall thickness of 0.20 mm-0.60 mm, and a concentricity of 80%-100%; the manufacture of the balloon involving heating the initial tube to reach a glass transition temperature, inflating the initial tube and stretching the initial tube to shape in a mold; wherein, in the manufacture of the balloon, the initial tube bears a stretching rate of 150%-400% and an inflation ratio of 2.5-4.0.

2. The balloon catheter according to claim 1, wherein the nominal dilation pressure of the balloon is 3 atm.

3. The balloon catheter according to claim 1, wherein the rated burst pressure of the balloon catheter is 12 atm.

4. The balloon catheter according to claim 1, wherein the balloon adopts a folding structure of two folded wings, three folded wings or five folded wings, with a crossing profile of 0.66 mm-0.90 mm.

5. The balloon catheter according to claim 4, wherein the crossing profile of the balloon is 0.78 mm.

6. The balloon catheter according to claim 1, wherein the length of a coaxial structure of a hose section of the balloon catheter is 300-400 mm.

7. The balloon catheter according to claim 1, wherein the push member is composed of a metal-based hypo tube or a braided tube with a cavity structure, the push member has a length of 800 mm-1400 mm, an outer diameter of 0.40 mm-0.70 mm, and a thickness of 0.05 mm-0.15 mm, the transition member is selected from a hypo tube with a screw structure and a core wire with a variable diameter structure, and materials of the outer tube and the inner tube are selected from a block polyether amide elastomer, nylon, polyurethane or HDPE.

8. The balloon catheter according to claim 1, wherein the transition member is of a spiral cut structure made of metal, and an end of the transition member forms a shovel shaped structure having gradually varied size.

9. The balloon catheter according to claim 1, wherein the imaging mark is provided on the inner tube, and material of the imaging mark is selected from gold, platinum, platinum iridium alloy and tungsten rhenium alloy.

* * * * *